US008513499B2

(12) United States Patent
Rooney et al.

(10) Patent No.: US 8,513,499 B2
(45) Date of Patent: Aug. 20, 2013

(54) **PLANTS AND SEEDS OF *SORGHUM* LINE TX3361**

(75) Inventors: William L. Rooney, College Station, TX (US); Leslie C. Kuhlman, Lawrence, KS (US)

(73) Assignee: The Texas A&M University System, College Station, TX (US)

( * ) Notice: Subject to any disclaimer, the term of this patent is extended or adjusted under 35 U.S.C. 154(b) by 905 days.

(21) Appl. No.: 12/508,885

(22) Filed: Jul. 24, 2009

(65) Prior Publication Data

US 2010/0064382 A1 Mar. 11, 2010

Related U.S. Application Data

(60) Provisional application No. 61/103,085, filed on Oct. 6, 2008, provisional application No. 61/083,436, filed on Jul. 24, 2008.

(51) Int. Cl.
*A01H 5/00* (2006.01)
*C12N 15/82* (2006.01)

(52) U.S. Cl.
USPC ............ 800/320; 800/260; 800/278; 435/410

(58) Field of Classification Search
USPC ....................................................... 800/320
See application file for complete search history.

(56) References Cited

FOREIGN PATENT DOCUMENTS

| CN | 1802441 A | 7/2006 |
|---|---|---|
| CN | 101037639 A | 9/2007 |
| WO | WO 2004/090171 | 10/2004 |

OTHER PUBLICATIONS

Bourne, "A comparative study of certain morphological characters of surgarcane X sorgo hybrids," *J. Agric. Res.*, 50:539-552, 1935.
Bower et al., "High-efficiency, microprojectile-mediated cotransformation of sugarcane, using visible or selectable markers," *Molecular Breeding*, 2:239-249, 1996.
De Wet et al., "Cytogenetics of introgression from *Saccharum* into *Sorghum*," *Crop Sci.*, 16:568-572, 1976.
Gallo-Meagher et al., "Herbicide resistant transgenic sugarcane plants containing the bar gene," *Crop Sci.*, 36:1367-1374, 1996.
Gupta et al., "Morphology of *Saccharum-Sorghum* hybrid derivatives," *Amer. J. Bot.*, 65(9):936-942, 1978.
Hodnett et al., "Pollen-pistil interactions result in reproductive isolation between *Sorghum* bicolor and divergent *Sorghum* species," *Crop Sci.*, 45:1403-1409, 2005.
Howe et al., "Rapid and reproducible *Agrobacterium*-mediated transformation of *Sorghum*," *Plant Cell Rep.*, 25:784-791, 2006.
Kuhlman et al., "Genetic recombination in *Sorghum* bicolor x *S. macrospermum* interspecific hybrids," *Genome*, 51:749-756, 2008.
Kuhlman, "*Sorghum* Introgression Breeding Utilizing *S. macrospermum*," Ph.D. Dissertation, Texas A&M University, Aug. 2007.
Laurie et al., "Genetic variation in *Sorghum* for the inhibition of maize pollen tube growth," *Annals of Botany*, 64:675-681, 1989.
Lo et al., "Breeding of *Saccharum*-miscanthus hybrids for fibre resource," Proceedings XX Congress, pp. 892-898, International Society of Sugar Cane Technologists, Thompson (Ed.), The Organizing Committee of the XX ISSCT Congress, Sao Paulo, Brazil, Oct. 12-21, 1989.
Moriya, "Contributions to the cytology of genus *Saccharum* I. Observations on the F1 progeny of sugar cane-sorghum hybrids," *Cytologia*, 11:117-135, 1940.
Nair, "Production and cyto-morphological analysis of intergeneric hybrids of *Sorghum* X *Saccharum*," *Euphytica*, 108:187-191, 1999.
Nair et al., "Characterization of intergeneric hybrids of *Saccharum* using molecular markers," *Genetic Resources and Crop Evolution*, 53:163-169, 2006.
Paterson et al., "Ancient polyploidization predating divergence of the cereals, and its consequences for comparative genomics," *PNAS*, 101(26):9903-9908, 2004.
Price et al., "Genotype dependent interspecific hybridization of *Sorghum* bicolor," *Crop Sci.*, 46:2617-2622, 2006.
Rooney et al., "Designing *Sorghum* as a dedicated bioenergy feedstock," *Biofuels, Bioproducts and Biorefining*, 1(2):147-157, 2007.
Terajima et al., "The simultaneous production of sugar and biomass ethanol using high-biomass surgarcane derived from interspecific and inter-generic cross in Japan," Proceedings of Biomass Asia Workshop 2, pp. 65, Bangkok, Thailand, Dec. 13-15, 2005.
Venkatraman, "Sugarcane-*Sorghum* hybrids. Part I General outline and early characters," *Ind J. Agric. Sci.*, 2:19-27, 1932.
James, "New types of maize X *Tripsacum* and maize x *Sorghum* hybrids—their use in maize improvement," Proceedings of the tenth meeting of the Maize and Sorghum Section of Eucarpia, European Assoc. For Res. on Plant Breedings, Varna, Sep. 17-19, 1979.
Kuhlman et al., "Registration of Tx3361 *Sorghum* Germplasm", Journal of Plant Registrations, 5:133-134, 2011.

*Primary Examiner* — Li Zheng
(74) *Attorney, Agent, or Firm* — Dentons US LLP

(57) ABSTRACT

According to the invention, there is provided seed and plants of the *sorghum* line designated Tx3361. The invention thus relates to the plants, seeds and tissue cultures of the line Tx3361, and to methods for producing a plant produced by crossing a *sorghum* plant of line Tx3361 with itself or with another plant, such as a plant of another line, species or genus. The invention further relates to seeds and plants produced by crossing plants of line Tx3361 with plants of another line, species or genus. The invention further relates to the inbred and hybrid genetic complements of plants of line Tx3361.

23 Claims, No Drawings

PLANTS AND SEEDS OF SORGHUM LINE TX3361

This application claims priority to U.S. Provisional Application No. 61/103,085, filed on Oct. 6, 2008, and to U.S. Provisional Application No. 61/083,436, filed on Jul. 24, 2008. The foregoing applications are incorporated herein by reference in their entirety.

This invention was made with government support under CSREES National Research Initiative grant number 2004-35300-14686 awarded by the U.S. Department of Agriculture (USDA). The United States government has certain rights in the invention.

BACKGROUND OF THE INVENTION

1. Field of the Invention

The present invention relates generally to the field of sorghum breeding. In particular, the invention relates to sorghum seed and plants of the line designated Tx3361, and derivatives and tissue cultures thereof.

2. Description of Related Art

The goal of field crop breeding is to combine various desirable traits in a single variety/hybrid. Such desirable traits include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Sorghum plants (Sorghum bicolor L.) can be bred by both self-pollination and cross-pollination but self-pollination is the typical mode of reproduction for the sorghum species. Both types of pollination involve the sorghum plant's flowers. Sorghum has a perfect flower with both male and female parts in the same flower located in the panicle. The flowers are usually in pairs on the panicle branches. Natural pollination occurs in sorghum when anthers (male flowers) open and pollen falls onto receptive stigma (female flowers). Because of the close proximity of male and female in the panicle, self-pollination is very high. Cross-pollination of sorghum also occurs when wind or convection currents move pollen from the anthers of one plant to receptive stigma on another plant.

Plants that have been self-pollinated and selected for type over many generations become homozygous at almost all gene loci and produce a uniform population of true breeding progeny, a homozygous plant. A cross between two such homozygous plants produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform sorghum plant hybrids requires the development of homozygous inbred plants, the crossing of these inbred plants, and the evaluation of the crosses. Pedigree breeding and recurrent selection are examples of breeding methods used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

A continuing goal of sorghum breeding programs is to develop sorghum hybrids that are based on stable inbred plants and have one or more desirable characteristics. To accomplish this goal, the sorghum breeder must select and develop superior inbred parental plants.

SUMMARY OF THE INVENTION

In one aspect, the present invention provides a cell comprising at least a first set of chromosomes of the sorghum line designated Tx3361. In one embodiment, the cell is a cell of sorghum line Tx3361. The invention also relates to plants and seeds comprising a cell of sorghum line Tx3361. In another aspect, the invention further provides for plants produced by growing the seed of the sorghum line Tx3361, as well as the derivatives of such plants. Also provided are sorghum plants having all the physiological and morphological characteristics of the sorghum line Tx3361. A sorghum plant of the invention may further comprise, or have, a cytoplasmic or nuclear factor that is capable of conferring male sterility or otherwise preventing self-pollination, such as by self-incompatibility. Parts of the sorghum plant of the present invention are also provided, for example, protoplast, cell, meristem, root, pistil, anther, flower, seed, embryo, stalk or petiole.

The invention also concerns seed of the sorghum line Tx3361. The seed of the invention may be provided, in one embodiment, as an essentially homogeneous population of sorghum seed of the line designated Tx3361. Essentially homogeneous populations of inbred seed are generally free from substantial numbers of other seed. The seed population may be separately grown to provide an essentially homogeneous population of sorghum plants designated Tx3361.

In another aspect of the invention, a plant of sorghum line Tx3361 comprising an added heritable trait is provided. The heritable trait may comprise a genetic locus that is a dominant or recessive allele. In one embodiment of the invention, a plant of sorghum line Tx3361 comprising a single locus conversion is provided. In specific embodiments of the invention, an added genetic locus confers a trait such as, for example, herbicide tolerance, insect resistance, disease resistance, waxy starch, modified fatty acid metabolism, modified phytic acid metabolism, modified carbohydrate metabolism, modified protein metabolism, drought tolerance, increased biomass, enhanced sugar production, sugar content, cellulose content and perennial growth habit. The trait may be, for example, conferred by a naturally occurring sorghum gene introduced into the genome of the variety by backcrossing, a natural or induced mutation, a transgene introduced through genetic transformation techniques directly into the line or via backcrossing from another plant that has been genetically transformed. When introduced through transformation, a genetic locus may comprise one or more transgenes integrated at a single chromosomal location.

In yet another aspect of the invention, a sorghum plant of the line designated Tx3361 is provided, wherein a cytoplasmically-inherited trait has been introduced into said plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer alleles in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continues to be male sterile in the next generation. The male fertility of a CMS plant can be restored by a restorer version of the same variety, which must have the restorer gene(s) in the nucleus. With the restorer gene(s) in the nucleus, the offspring of the male-sterile plant can produce normal pollen grains and propagate. A cytoplasmically inherited trait may be a naturally occurring *sorghum* trait or a trait produced through genetic transformation techniques.

In another aspect of the invention, a tissue culture of regenerable cells of a plant of line Tx3361 is provided. The tissue culture may be capable of regenerating plants capable of expressing all of the physiological and morphological characteristics of the line. The tissue culture may regenerate plants having substantially the same genotype as other plants of the line. Examples of some of the physiological and morphological characteristics of the line Tx3361 include characteristics related to yield, maturity, male sterility, drought tolerance and sugar content, each of which is specifically disclosed herein. The regenerable cells in such tissue cultures can be derived from embryos, meristematic cells, microspores, pollen, leaves, anthers, roots, root tips, silk, flowers, kernels or stalks, or from callus or protoplasts derived from those tissues. Still further, the present invention provides *sorghum* plants regenerated from a tissue culture of the invention, the plants having all the physiological and morphological characteristics of line Tx3361.

In yet another aspect of the invention, processes are provided for producing seeds or plants, which processes generally comprise crossing a first parent plant with a second parent plant, wherein at least one of the first or second parent plants is a plant of the line designated Tx3361. These processes may be further exemplified as processes for preparing hybrid *sorghum* seed or plants, wherein a first *sorghum* plant is crossed with a second *sorghum* plant of a different, distinct variety to provide a hybrid that has, as one of its parents, the *sorghum* plant line Tx3361. In these processes, crossing will result in the production of seed. The seed production occurs regardless of whether the seed is collected or not.

In certain aspects the invention also provides processes for producing intergeneric or interspecific hybrids. This process generally comprises crossing a first plant according to the invention with a second plant of a different species or genera. The invention thus also provides intergeneric and interspecific plants having as one parent a plant of line Tx3361.

In one embodiment of the invention, a first step in "crossing" comprises planting, preferably in pollinating proximity, seeds of a first and second parent plant, at least one of which is line Tx3361. Alternatively, pollen can be transferred manually.

A second step may comprise cultivating or growing the seeds of said first and second parent plants into plants. A third step may comprise selfing that plant. Alternatively, another step may comprise preventing self-pollination of the plant. This can be done by emasculating the male flowers of the first or second parent plant, (i.e., treating or manipulating the flowers so as to prevent pollen production, in order to produce an emasculated parent plant). Self-incompatibility systems may also be used for the same purpose. Self-incompatible plants still shed viable pollen and can pollinate plants of other varieties but are incapable of pollinating themselves or other plants of the same variety.

Yet another step may comprise harvesting the seeds from at least one of the parent plants. The harvested seed can be grown to produce a *sorghum* plant or, in the case of cross-pollination, a hybrid plant.

The present invention also provides seeds and plants produced by a process that comprises crossing a first parent plant with a second parent plant, wherein at least one of the first or second parent plants is a plant of the line designated Tx3361. In one embodiment of the invention, seeds and plants produced by the process are first generation ($F_1$) hybrid *sorghum* seeds and plants produced by crossing a *sorghum* plant in accordance with the invention with another, distinct *sorghum* plant. The present invention further contemplates intergeneric or interspecific plants and seed therefrom. Therefore, certain exemplary embodiments of the invention provide an $F_1$ hybrid plants and seeds thereof.

In still yet another aspect of the invention, the genetic complement of the *sorghum* plant line designated Tx3361 is provided. The phrase "genetic complement" is used to refer to the aggregate of nucleotide sequences, the expression of which sequences defines the phenotype of, in the present case, a *sorghum* plant, or a cell or tissue of that plant. A genetic complement thus represents the genetic make up of an inbred cell, tissue or plant, and a hybrid genetic complement represents the genetic make up of a hybrid cell, tissue or plant. The invention thus provides *sorghum* plant cells that have a genetic complement in accordance with the *sorghum* plant cells disclosed herein, and plants, seeds and diploid plants containing such cells. Such cells, seeds and plants may be defined as comprising a haploid set of chromosomes of a plant line Tx3361, including any higher ploidy levels thereof capable of being produced.

Plant genetic complements may be assessed by genetic marker profiles, and by the expression of phenotypic traits that are characteristic of the expression of the genetic complement, e.g., isozyme typing profiles. It is understood that *sorghum* line Tx3361 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by *sorghum* plant cells, tissues, plants, and seeds, formed by the combination of a haploid genetic complement of a *sorghum* plant of the invention with a haploid genetic complement of a second plant. In another aspect, the present invention provides a *sorghum* plant regenerated from a tissue culture that comprises a hybrid genetic complement of this invention.

In still yet another aspect, the present invention provides a method of producing a *sorghum* plant derived from the *sorghum* line Tx3361, the method comprising the steps of: (a) preparing a progeny plant derived from *sorghum* line Tx3361, wherein said preparing comprises crossing a plant of the *sorghum* line Tx3361 with a second plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating the steps for an additional 3-10 generations to produce a *sorghum* plant derived from the *sorghum* line Tx3361. In the method, it may be desirable to select particular plants resulting from step (c) for continued crossing according to steps (b) and (c). By selecting plants having one or more desirable traits, a *sorghum* plant derived from the *sorghum* line Tx3361 is obtained which possesses some of the desirable traits of *sorghum* line Tx3361 as well potentially other selected traits.

DETAILED DESCRIPTION OF THE INVENTION

I. Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a *sorghum* plant, thereby resulting in the production of seed from the flower.

Cross-pollination: Fertilization by the union of two gametes from different plants.

Diploid: A cell or organism having two sets of chromosomes.

Emasculate: The removal of plant male sex organs or the inactivation of the organs with a chemical agent or a cytoplasmic or nuclear genetic factor conferring male sterility.

$F_1$ Hybrid: The first generation progeny of the cross of two plants.

Genetic Complement: An aggregate of nucleotide sequences, the expression of which sequences defines the phenotype in *sorghum* plants, or components of plants including cells or tissue.

Genotype: The genetic constitution of a cell or organism.

Haploid: A cell or organism having one set of the two sets of chromosomes in a diploid.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR™ amplification using flanking oligonucleotide primers.

Self-pollination: The transfer of pollen from the anther to the stigma of the same plant.

Single Locus Converted (Conversion) Plant: Plants which are developed by a plant breeding technique called backcrossing wherein essentially all of the desired morphological and physiological characteristics of an inbred are recovered in addition to the characteristics conferred by the single locus transferred into the inbred via the backcrossing technique.

Tissue Culture: A composition comprising isolated cells of the same or a different type or a collection of such cells organized into parts of a plant.

Transgene: A genetic sequence which has been introduced into the nuclear or chloroplast genome of a *sorghum* plant by a genetic transformation technique.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

II. *Sorghum* Line Tx3361

A. Origin and Breeding History

*Sorghum* line Tx3361 is homozygous recessive at the iap (Inhibition of Alien Pollen) locus and segregates for genetic male sterility at the $Ms_3$ locus. Genetic segregation at the $Ms_3$ locus results in a high frequency of genetic male sterile plants that can be used to make hybrids without needing emasculation.

Line Tx3361 was derived from an initial cross between the genetic male-sterile line BTx623 ms3 and line NR481. Line BTx623 ms3 contains the ms3 allele for genetic male-sterility and line NR481 is homozygous for the iap allele (Laurie and Bennett, 1989). The origin and breeding history of plant Tx3361 can be summarized as follows:

An original cross was made between parent lines BTx623 ms3 and NR481. The hybrid was backcrossed once to the BTx623 ms3 parent. Fertile $BC_1F_1$ progeny were self-pollinated and selected for 3-dwarf height, white pericarp, no awns, absence of pigmented testa, and reduced lodging in College Station, Tex. $BC_1F_2$ progeny were grown in a greenhouse, hand emasculated and tested for maize pollen tube growth (Laurie and Bennett, 1989). Genotypes at the iap locus were based on qualitatively measuring maize pollen tube growth to the base of the style in *sorghum* pistils 24 hours after pollination. Individuals that show maize pollen tube growth to the base of the style are considered iap/iap. Selected iap/iap individuals were self-pollinated and progeny rows were grown the following season in College Station, Tex. Lines were evaluated for lodging, height, awns and segregation of the ms3 allele. Selected male-fertile and sterile plants ($BC_1F_3$) within ms3 segregating rows were sib-mated. Individual sib crosses were grown in Weslaco, Tex. and evaluated for stable backcross segregation of ms3, lodging, height and maturity. Maize pollen tube growth was used to confirm iap locus genotype. The selected line was bulk sib-mated between male-sterile and fertile plants to produce breeder's seed of the proposed genetic stock. The selected line is a maintainer of sterility and the A1 cytoplamic male sterility system.

In one embodiment, this genetic stock can be used as a female parent to obtain interspecific crosses with exotic *sorghum* species or intergeneric crosses.

*Sorghum* plants can be reproduced by planting the seeds of *sorghum* line Tx3361 and growing the resulting *sorghum* plants under self-pollinating or sib-pollinating conditions with adequate isolation using standard techniques well known to an artisan skilled in the agricultural arts. Seeds can be harvested from such a plant using standard, well known procedures.

B. Phenotypic Description

In accordance with one aspect of the present invention, there is provided a *sorghum* plant having the physiological and morphological characteristics of *sorghum* line Tx3361. A description of the physiological and morphological characteristics of *sorghum* line Tx3361 is presented in Table 1.

TABLE 1

Physiological and Morphological Traits for *Sorghum* Line Tx3361

| CHARACTERISTIC | Tx3361 |
|---|---|
| 1. General | |
| Kind | *Sorghum* |
| Inbred Type | Parental Line |
| Male Sterile Cytoplasm | Maintainer of A1, A2 and A3 Cytoplasm |
| Use Class | Grain |
| 2. Maturity | |
| Days from Planting to Mid-Anthesis | 63 |
| Number of Days Earlier Than TX430 | 7 |
| 3. Plant | |
| Coleptile | Green |
| Plant Pigment | Purple |
| 4. Stalk | |
| Diameter | Mid-Stout |
| 5. Stalk Height | |
| cm From Soil to Top of Plant | 112 |
| cm Greater Than RTx437 | 25 |
| No. of Recessive Height Genes | 3 |
| Plant Height Genotype (Recessive) | dw1 Dw2 dw3 dw4 |
| Waxy Bloom | Present |
| Tillers | Moderate |
| Sweetness | Insipid |
| Juiciness | Dry (Pithy) |
| Panicle Exsertion | Medium |
| Degree of Senescence | Intermediate |
| 6. Leaf | |
| Width (Relative to Class) | Moderate |
| Color | Dark Green |
| Margin | Smooth |
| Attitude | Horizontal |
| Ligule | Present |
| Midrib Color | White |
| 7. Panicle | |
| Anther Color (At Flowering) | Light Yellow |
| cm Panicle Length | 30 |
| cm Greater Than RTx437 | 5 |
| Density | Semi-Open |
| Shape | Oval |
| Length of Central Rachis (% of Panicle Length) | 75% |
| Rachis Branches (At Grain Maturity) | Horizontal |
| Rachis Branch Average Glumes | Intermediate |
| Length | Intermediate |
| % of Grain Covered by Glume | 25% |

TABLE 1-continued

Physiological and Morphological Traits for *Sorghum* Line Tx3361

| CHARACTERISTIC | Tx3361 |
|---|---|
| Texture | Intermediate |
| Color (At Grain Maturity) | Light Tan |
| Hairiness | Smooth |
| Venation | Present |
| Transverse Wrinkle | Absent |
| Awns | Absent |
| 8. Roots | |
| Roots | Fibrous |
| 9. Grain | |
| Testa | Absent |
| Mesocarp Thickness | Thick |
| Epicarp Color (Genetic) | White |
| Grain Color (Appearance) | White Chalky (Opaque) |
| Endosperm Color | White |
| Endosperm Type | Starchy |
| Endosperm Texture | Intermediate |
| Seed Shape | Oval |
| 10. Insect Resistance | |
| *Sorghum* Midge | Susceptible |

*These are typical values. Values may vary due to environment. Other values that are substantially equivalent are also within the scope of the invention.

C. Performance Characteristics

As described above, line Tx3361 exhibits desirable agronomic traits. The performance characteristics of line Tx3361 were the subject of an objective analysis of the performance traits relative to other varieties. The results of the analysis are presented below.

TABLE 2

Performance Characteristics for *Sorghum* Line Tx3361 and Selected Varieties

| | NR481 | BTx623ms3 | Tx3361 | LSD$_{(.05)}$ |
|---|---|---|---|---|
| Dwarf Loci | __dw2___* | dw1 Dw2 dw3 dw4 | dw1 Dw2 dw3 dw4 | |
| Pericarp Color | Red | White | White | |
| Awns | Yes | No | No | |
| Pigmented Testa | Yes | No | No | |
| ms3 Backcross Segregation | No | Yes | Yes | |
| Maize PTG | 22.5%$^A$ | 0.0%$^B$ | 15.3%$^A$ | 11.0% |
| iap Locus | iap/iap | Iap/Iap | iap/iap | |
| Height (in.) | 92$^A$ | 54$^B$ | 54$^B$ | 7.5 |
| Exsertion (in.) | 8.3$^A$ | 3.6$^B$ | 4.5$^B$ | 2.8 |
| Lodging | 5.7$^A$ | 0.6$^B$ | 1.8$^B$ | 1.5 |
| Days to 50% Anthesis | 49$^C$ | 65$^A$ | 53$^B$ | 3.5 |

*NR481 has 2 loci that are homozygous recessive but only the genotype at Dw2 is known.
Values are means, different letters within rows indicate significantly different means a = .05.
Dwarf Loci: represents the homozygous allele at each dwarfing locus.
Maize PTG: represents the frequency of *sorghum* pistils with maize pollen tube growth to the base of the style.
Lodging: 0-9 scale, 0 = 0-10%, 9 = 90-100% lodging.

D. Deposit Information

A deposit was made of at least 2500 seeds of *sorghum* line Tx3361 with the American Type Culture Collection (ATCC), 10801 University Boulevard, Manassas, Va. 20110-2209 USA. The deposit was assigned ATCC Accession No. PTA-10149. The date of deposit of the seeds with the ATCC was Jun. 25, 2009. Access to this deposit will be available during the pendency of the application to the Commissioner of Patents and Trademarks and persons determined by the Commissioner to be entitled thereto upon request. The deposit will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent or under the Plant Variety Protection Act (7 U.S.C. 2321 et seq.).

III. Further Embodiments of the Invention

A. Breeding *Sorghum* Line Tx3361

One aspect of the current invention concerns methods for crossing the *sorghum* line Tx3361 with itself or a second plant and the seeds and plants produced by such methods. These methods can be used for propagation of the *sorghum* line Tx3361, or can be used to produce hybrid seeds and the plants grown therefrom. A hybrid plant can be used as a recurrent parent at any given stage in a backcrossing protocol during the production of a single locus conversion of the *sorghum* line Tx3361.

The line of the present invention is well suited to the development of new varieties. For example, a *sorghum* plant Tx3361 could be crossed to any second plant, and the resulting hybrid progeny each selfed for about 5 to 7 or more generations, thereby providing a large number of distinct, pure-breeding inbred lines. These inbred lines could then be crossed with other inbred or non-inbred lines and the resulting hybrid progeny analyzed for beneficial characteristics. In this way, novel inbred lines conferring desirable characteristics could be identified.

In selecting a second plant to cross with Tx3361 for the purpose of developing novel *sorghum* varieties, it will typically be desired to choose those plants which themselves exhibit one or more selected desirable characteristics. Examples of potentially desired characteristics include male sterility, waxy starch, herbicide resistance, resistance for bacterial, fungal, or viral disease, insect resistance, male fertility, enhanced nutritional quality, drought tolerance, increased biomass, enhanced sugar production, sugar content, cellulose content and perennial growth habit.

Any time the *sorghum* line Tx3361 is crossed with another, different, variety, first generation ($F_1$) progeny are produced. The hybrid progeny are produced regardless of characteristics of the two varieties produced. As such, an $F_1$ hybrid plant may be produced by crossing Tx3361 with any second plant capable of being crossed to Tx3361. The second plant may be genetically homogeneous (e.g., inbred) or may itself be a hybrid. Therefore, any $F_1$ hybrid plant produced by crossing *sorghum* line Tx3361 with a second plant is a part of the present invention.

*Sorghum* plants can be crossed by either natural or mechanical techniques. Natural pollination occurs in *sorghum* when pollen falls or is blown from the anther to the stigma of the flowers.

The *sorghum* flower is monecious in that the male and female structures are in the same flower. The crossed or hybrid seed can be produced by manual crosses between selected parents. Floral buds of the parent that is to be the female can be emasculated prior to the opening of the flower by manual removal of the male anthers. At flowering, the pollen from flowers of the parent plants designated as male, can be manually placed on the stigma of the previous emasculated flower. Seeds developed from the cross are $F_1$ hybrid seeds. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

Self-pollination occurs naturally in *sorghum* with no manipulation of the flowers. For the crossing of two *sorghum* plants, it is typically preferable to utilize artificial hybridization. In artificial hybridization, the flower used as a female in a cross is manually cross-pollinated prior to maturation of pollen from the flower, thereby preventing self fertilization, or alternatively, the male parts of the flower are emasculated using a technique known in the art. Techniques for emasculating the male parts of a *sorghum* flower include, for example, physical removal of the male parts, use of a genetic factor conferring male sterility, and application of a chemical gametocide to the male parts.

Following emasculation, the plants are then typically allowed to continue to grow and natural cross-pollination occurs as a result of the action of wind, which is normal in the pollination of grasses, including *sorghum*. As a result of the emasculation of the female parent plant, all the pollen from the male parent plant is available for pollination because pollen bearing flowering parts (anthers) have been previously removed from all plants being used as the female in the hybridization. Of course, during this hybridization procedure, the parental varieties are grown such that they are isolated from other *sorghum* fields to minimize or prevent any accidental contamination of pollen from foreign sources. These isolation techniques are well within the skill of those skilled in this art.

Either with or without emasculation of the female flower, hand pollination can be carried out by removing the stamens and pistil with a forceps from a flower of the male parent and gently brushing the anthers against the stigma of the female flower. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Both parental plants may be allowed to continue to grow until maturity or the male rows may be destroyed after flowering is complete. The novel $F_1$ hybrid seeds are harvested and can then be planted in a subsequent growing season in commercial fields or, alternatively, advanced in breeding protocols for purposes of developing novel inbred lines.

Alternatively, in another embodiment of the invention, both first and second parent *sorghum* plants can be from variety Tx3361. Thus, any *sorghum* plant produced using *sorghum* plant Tx3361 forms a part of the invention. As used herein, crossing can mean selfing, backcrossing, crossing to another or the same inbred, crossing to populations, and the like. All plants produced using the *sorghum* plant Tx3361 as a parent are, therefore, within the scope of this invention.

B. Intergeneric or Interspecific Hybrid Production

In certain aspects the invention provides methods for producing intergeneric or interspecific hybrids derived from the cross of a plant of line Tx3361 and a second plant from a different genus or species than line Tx3361. In such hybrid crosses, there is a pollen recipient plant or female plant as a parent, as well as a pollen donor plant or male parent as another parent, although it will be recognized that each parent may possess male and female flowers.

In certain embodiments, examples of genera that include species to be included in intergeneric or interspecific crosses include, but are not limited to *Sorghum*, sugarcane (*Saccharum*) and *Miscanthus*. Plants of these species have been identified as potential biofuel crops and the creation of hybrid plants with line Tx3361 as a one parent and a sugarcane,

*Miscanthus* or *Sorghum* of a different species as a second parent would be extremely valuable for crop improvement programs.

To create such hybrid plants it is necessary to overcome interspecific and/or intergeneric reproductive barriers among these grass species. It is disclosed by certain aspects of this invention that the reproductive barriers between many of the currently proposed biofuel crops can be circumvented through utilization of the *sorghum* mutant gene iap. *Sorghum* plants of line Tx3361 are homozygous for the iap allele and therefore are receptive to pollen from plants of other species and genera thus providing potential to create intergeneric and interspecific hybrids.

C. $F_1$ Hybrid Plant and Seed Production

One beneficial use of *sorghum* line Tx3361 is in the production of hybrid seed. Essentially any other plant sexually compatible with line Tx3361 can be used to produce a hybrid plant having *sorghum* plant Tx3361 as one parent.

The goal of the process of producing an $F_1$ hybrid is to manipulate the genetic complement of *sorghum* to generate new combinations of genes which interact to yield new or improved traits (phenotypic characteristics). A process of producing an $F_1$ hybrid often begins with the production of one or more inbred plants. Those plants are produced by repeated crossing of ancestrally related plants to try to combine certain genes within the inbred plants.

*Sorghum* has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

A single cross hybrid variety is the cross of two inbred plants, each of which has a genotype which complements the genotype of the other. Typically, $F_1$ hybrids are more vigorous than their inbred parents. This hybrid vigor, or heterosis, is manifested in many polygenic traits, including markedly improved yields, better stalks, better roots, better uniformity and better insect and disease resistance. In the development of hybrids only the $F_1$ hybrid plants are typically sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

Any one of the numerous *sorghum* varieties known in the art could be crossed with *sorghum* plant Tx3361 to produce a hybrid plant.

When the *sorghum* plant Tx3361 is crossed with another plant to yield a hybrid, it can potentially serve as either the maternal or paternal plant. In the case of hybrids with a plant other than a *sorghum* plant, Tx3361 will generally serve as the female parent in view of the presence of the iap allele. Depending on the seed production characteristics relative to a second parent in a hybrid cross, it may be desired to use one of the parental plants as the male or female parent. Seed coat characteristics can be preferable in one plant. Pollen can be shed better by one plant. Therefore, a decision to use one parent plant as a male or female may be made based on any such characteristics as is well known to those of skill in the art.

D. Development of Varieties

The development of new varieties using one or more starting varieties is well known in the art. In accordance with the invention, novel varieties may be created by crossing *sorghum* line Tx3361 followed by multiple generations of breeding according to such well known methods. New varieties may be created by crossing *sorghum* line Tx3361 with any second plant. In selecting such a second plant to cross for the purpose of developing novel inbred lines, it may be desired to choose those plants which either themselves exhibit one or more selected desirable characteristics or which exhibit the desired characteristic(s) when in hybrid combination. Examples of potentially desired characteristics include greater yield, better stalks, better roots, resistance to insecticides, herbicides, pests, and disease, tolerance to heat and drought, reduced time to crop maturity, better agronomic quality, higher nutritional value, and uniformity in germination times, stand establishment, growth rate, maturity, and fruit size.

Once initial crosses have been made with *sorghum* line Tx3361, inbreeding takes place to produce new inbred varieties and generate a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $F_1 \rightarrow F_2$; $F_2 \rightarrow F_3$; $F_3 \rightarrow F_4$; $F_4 \rightarrow F_5$, etc. After at least five generations, the inbred plant is considered genetically pure.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The development of a hybrid *sorghum* variety involves three steps: (1) the selection of plants from various germplasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in *sorghum*, the vigor of the plants decreases to some extent. Vigor is restored when two unrelated inbred plants are crossed to produce the hybrid progeny ($F_1$). An important consequence of the homozygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids.

During the next several years, a progressive elimination of hybrids occurs based on more detailed evaluation of their phenotype. Eventually, trials are conducted to formally compare the experimental hybrids being developed with other hybrids, some of which were previously developed and generally are commercially successful. That is, comparisons of experimental hybrids are made to competitive hybrids to determine if there was any advantage to further development of the experimental hybrids. After trials are complete, determinations may be made whether commercial development should proceed for a given hybrid.

E. $F_1$ Hybrid Comparisons

As mentioned above, hybrids are progressively eliminated following detailed evaluations of their phenotype, including formal comparisons with other commercially successful hybrids. Strip trials are used to compare the phenotypes of hybrids grown in as many environments as possible. They are performed in many environments to assess overall performance of the new hybrids and to select optimum growing conditions. Because the *sorghum* is grown in close proximity, environmental factors that affect gene expression, such as moisture, temperature, sunlight, and pests, are minimized. For a decision to be made to commercialize a hybrid, it is not necessary that the hybrid be better than all other hybrids. Rather, significant improvements must be shown in at least some traits that would create improvements in some niches.

F. Production of Plants with Desired Traits

In certain further aspects, the invention provides plants modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene. It is understood that a locus introduced by backcrossing may or may not be transgenic in origin, and thus the term backcrossing specifically includes backcrossing to introduce loci that were created by genetic transformation.

As described above, backcrossing methods can be used with the present invention to improve or introduce a trait into a variety. The term backcrossing as used herein refers to the repeated crossing of a hybrid progeny back to one of the parental *sorghum* plants. The parental *sorghum* plant which contributes the locus or loci for the desired trait is termed the nonrecurrent or donor parent. This terminology refers to the fact that the nonrecurrent parent is used one time in the backcross protocol and therefore does not recur.

The parental *sorghum* plant to which the locus or loci from the nonrecurrent parent are transferred is known as the recurrent parent as it is used for several rounds in the backcrossing protocol (Poehlman et al., 1995; Fehr, 1987; Sprague and Dudley, 1988). In a typical backcross protocol, the original parent of interest (recurrent parent) is crossed to a second variety (nonrecurrent parent) that carries the genetic locus of interest to be transferred. The resulting progeny from this cross are then crossed again to the recurrent parent and the process is repeated until a *sorghum* plant is obtained wherein essentially all of the desired morphological and physiological characteristics of the recurrent parent are recovered in the converted plant, in addition to the transferred locus from the nonrecurrent parent. The backcross process may be accelerated by the use of genetic markers, such as SSR, RFLP, SNP or AFLP markers to identify plants with the greatest genetic complement from the recurrent parent.

The selection of a suitable recurrent parent is an important step for a successful backcrossing procedure. The goal of a backcross protocol is to add or substitute one or more new traits in the original variety and progeny therefrom. To accomplish this, a genetic locus of the recurrent parent is modified or substituted with the desired locus from the nonrecurrent parent, while retaining essentially all of the rest of the desired genetic, and therefore the desired physiological and morphological constitution of the original plant. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, waxy starch, herbicide resistance, resistance for bacterial, fungal, or viral disease, insect resistance, male fertility, enhanced nutritional quality, drought tolerance, increased biomass, enhanced sugar production, sugar content, cellulose content and perennial growth habit. These genes are generally inherited through the nucleus, but may be inherited through the cytoplasm. Some known exceptions to this are genes for male sterility, some of which are inherited cytoplasmically, but may still act as a single locus trait.

Direct selection may be applied where a genetic locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

Many useful traits are those which are introduced by genetic transformation techniques. Methods for the genetic transformation of plants are known to those of skill in the art. For example, methods which have been described for the genetic transformation of plants include electroporation (U.S. Pat. No. 5,384,253), electrotransformation (U.S. Pat. No.

5,371,003), microprojectile bombardment (U.S. Pat. No. 5,550,318; U.S. Pat. No. 5,736,369, U.S. Pat. No. 5,538,880; and PCT Publication WO 95/06128), *Agrobacterium*-mediated transformation (U.S. Pat. No. 5,591,616 and E.P. Publication EP672752), direct DNA uptake transformation of protoplasts (Omirulleh et al., 1993) and silicon carbide fiber-mediated transformation (U.S. Pat. No. 5,302,532 and U.S. Pat. No. 5,464,765). In particular, methods for genetic transformation of *sorghum* by microprojectile bombardment are disclosed in Casas et al., 1993 and *Agrobacterium*-mediated transformation in U.S. Pat. No. 6,369,298.

It is understood to those of skill in the art that a transgene need not be directly transformed into a plant, as techniques for the production of stably transformed *sorghum* plants that pass single loci to progeny by Mendelian inheritance is well known in the art. Such loci may therefore be passed from parent plant to progeny plants by standard plant breeding techniques that are well known in the art. Non-limiting examples of traits that may be introduced into a *sorghum* plant or into a plant of a different genus or species according to specific embodiments of the invention include, but are not limited to, those conferring abiotic stress tolerance, drought tolerance, cold tolerance, heat tolerance, increased fertility, and those further detailed below.

1. Male Sterility

A series of nuclear recessive male sterility genes, designated as ms1 through ms7, have been characterized in *sorghum*. These mutations, in the recessive condition, result in a male-sterile plant that can be used for hybridization (Rooney, 2001). The use of nuclear male sterility genes is described in Pedersen and Toy, 1997. Male sterility genes can increase the efficiency with which hybrids are made, in that they eliminate the need to physically emasculate the *sorghum* plant used as a female in a given cross.

Where one desires to employ male-sterility systems with a *sorghum* plant in accordance with the invention, it may be beneficial to also utilize one or more male-fertility restorer genes. For example, where cytoplasmic male sterility (CMS) is used, hybrid seed production requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the *sorghum* plant is utilized, e.g., for silage, but in most cases, the seeds will be deemed the most valuable portion of the crop, so fertility of the hybrids in these crops must be restored. Therefore, one aspect of the current invention concerns plants of the *sorghum* line Tx3361 comprising a genetic locus capable of restoring male fertility in an otherwise male-sterile plant. Examples of male-sterility genes and corresponding restorers which could be employed with the plants of the invention are well known to those of skill in the art of plant breeding and are disclosed in, for instance, U.S. Pat. No. 5,530,191; U.S. Pat. No. 5,689,041; U.S. Pat. No. 5,741,684; and U.S. Pat. No. 5,684,242, the disclosures of which are each specifically incorporated herein by reference in their entirety.

2. Herbicide Resistance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988); Gleen et al., (1992) and Miki et al., (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. Examples of specific EPSPS transformation events conferring glyphosate resistance are provided by U.S. Pat. No. 6,040,497.

A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. DeGreef et al., (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acct-S1, Accl-S2 and Acct-S3 genes described by Marshall et al., (1992).

Genes are also known conferring resistance to a herbicide that inhibits photosynthesis, such as a triazine (psbA and gs+genes) and a benzonitrile (nitrilase gene). Przbila et al., (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., (1992).

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

3. Waxy Starch

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits additional progeny testing, for example growing additional generations such as the BC1S1, may be required to determine which plants carry the recessive gene.

4. Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to *Cladosporium fulvum*); Martin et al., (1993) (tomato Pto gene for resistance to *Pseudomonas syringae* pv. tomato); and Mindrinos et al., (1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody may also be used. See, for example, Tavladoraki et al., (1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730.

Logemann et al., (1992), for example, disclose transgenic plants expressing a barley ribosome-inactivating gene have an increased resistance to fungal disease. Other examples of fungal disease resistance are provided in U.S. Pat. Nos. 6,653,280; 6,573,361; 6,506,962; 6,316,407; 6,215,048; 5,516,671; 5,773,696; 6,121,436; 6,316,407; and 6,506,962).

Nematode resistance has been described, for example, in U.S. Pat. No. 6,228,992 and bacterial disease resistance in U.S. Pat. No. 5,516,671.

5. Insect Resistance

One example of an insect resistance gene includes a *Bacillus thuringiensis* protein, a derivative thereof or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor). An insect-specific hormone or pheromone may also be used. See, for example, the disclosure by Hammock et al., (1990), of baculovirus expression of cloned juvenile hormone esterase, an inactivator of juvenile hormone.

Still other examples include an insect-specific antibody or an immunotoxin derived therefrom and a developmental-arrestive protein. See Taylor et al., (1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

6. Modified Fatty Acid, Phytate and Carbohydrate Metabolism

Genes may be used conferring modified fatty acid metabolism, in terms of content and quality. For example, stearyl-ACP desaturase genes may be used. See Knutzon et al., (1992). Various fatty acid desaturases have also been described, such as a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (McDonough et al., 1992); a gene encoding a stearoyl-acyl carrier protein delta-9 desaturase from castor (Fox et al. 1993); Δ6- and Δ12-desaturases from the cyanobacteria *Synechocystis* responsible for the conversion of linoleic acid (18:2) to gamma-linolenic acid (18:3 gamma) (Reddy et al. 1993); a gene from *Arabidopsis thaliana* that encodes an omega-3 desaturase (Arondel et al. 1992)); plant Δ9-desaturases (PCT Application Publ. No. WO 91/13972) and soybean and *Brassica* Δ15 desaturases (European Patent Application Publ. No. EP 0616644).

Modified oils production is disclosed, for example, in U.S. Pat. Nos. 6,444,876; 6,426,447 and 6,380,462. High oil production is disclosed, for example, in U.S. Pat. Nos. 6,495,739; 5,608,149; 6,483,008 and 6,476,295. Modified fatty acid content is disclosed, for example, in U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al., (1993), for a disclosure of the nucleotide sequence of an *Aspergillus niger* phytase gene. In *sorghum*, this, for example, could be accomplished by cloning and then reintroducing DNA associated with the single allele which is responsible for *sorghum* mutants characterized by low levels of phytic acid.

A number of genes are known that may be used to alter carbohydrate metabolism. For example, plants may be transformed with a gene coding for an enzyme that alters the branching pattern of starch. See Shiroza et al., (1988) (nucleotide sequence of *Streptococcus mutans* fructosyltransferase gene), Steinmetz et al., (1985) (nucleotide sequence of *Bacillus subtilis* levansucrase gene), Pen et al., (1992) (production of transgenic plants that express *Bacillus licheniformis* α-amylase), U.S. Pat. No. 6,166,292 (low raffinose), Elliot et al., (1993) (nucleotide sequences of tomato invertase genes), Sergaard et al., (1993) (site-directed mutagenesis of barley α-amylase gene), Fisher et al., (1993) (maize endosperm starch branching enzyme II), and U.S. Pat. Nos. 6,538,181; 6,538,179; 6,538,178; 5,750,876 and 6,476,295 (starch content). The Z10 gene encoding a 10 kD zein storage protein from maize may also be used to alter the quantities of 10 kD zein in the cells relative to other components (Kirihara et al., 1988).

7. Illustrative Procedures for Introduction of a Desired Trait

As described above, techniques for the production of *sorghum* plants with added traits are well known in the art. A non-limiting example of such a procedure one of skill in the art would use for preparation of a *sorghum* plant of Tx3361 comprising an added trait is as follows:
(a) crossing *sorghum* plant Tx3361 to a second (nonrecurrent) *sorghum* plant comprising a locus to be converted in *sorghum* plant Tx3361;
(b) selecting at least a first progeny plant resulting from the crossing and comprising the locus;
(c) crossing the selected progeny to *sorghum* plant Tx3361; and
(d) repeating steps (b) and (c) until a plant of line Tx3361 is obtained comprising the locus.

Following these steps, essentially any locus may be introduced into *sorghum* line Tx3361. For example, molecular techniques allow introduction of any given locus, without the need for phenotypic screening of progeny during the backcrossing steps.

PCR and Southern hybridization are two examples of molecular techniques that may be used for confirmation of the presence of a given locus and thus conversion of that locus. The techniques are carried out as follows: Seeds of progeny plants are grown and DNA isolated from leaf tissue (see Sambrook et al., 2001; Shure et al. 1983). Approximately one gram of leaf tissue is lyophilized overnight in 15 ml polypropylene tubes. Freeze-dried tissue is ground to a powder in the tube using a glass rod. Powdered tissue is mixed thoroughly with 3 ml extraction buffer (7.0 urea, 0.35 M NaCl, 0.05 M Tris-HCl pH 8.0, 0.01 M EDTA, 1% sarcosine). Tissue/buffer homogenate is extracted with 3 ml phenol/chloroform. The aqueous phase is separated by centrifugation, and precipitated twice using 1/10 volume of 4.4 M ammonium acetate pH 5.2, and an equal volume of isopropanol. The precipitate is washed with 75% ethanol and resuspended in 100-500 µl TE (0.01 M Tris-HCl, 0.001 M EDTA, pH 8.0). The DNA may then be screened as desired for presence of the locus.

For PCR, two hundred to 1000 ng genomic DNA from the progeny plant being screened is added to a reaction mix containing 10 mM Tris-HCl pH 8.3, 1.5 mM $MgCl_2$, 50 mM KCl, 0.1 mg/ml gelatin, 200 µM each dATP, dCTP, dGTP, dTTP, 20% glycerol, 2.5 units Taq DNA polymerase and 0.5 µM each of forward and reverse DNA primers that span a segment of the locus being converted. The reaction is run in a thermal cycling machine 3 minutes at 94 C, 39 repeats of the cycle 1 minute at 94 C, 1 minute at 50 C, 30 seconds at 72 C, followed by 5 minutes at 72 C. Twenty µl of each reaction mix is run on a 3.5% NuSieve gel in TBE buffer (90 mM Tris-borate, 2 mM EDTA) at 50V for two to four hours. The amplified fragment is detected using an agarose gel. Detection of an amplified fragment corresponding to the segment of the locus spanned by the primers indicates the presence of the locus.

For Southern analysis, plant DNA is restricted, separated in an agarose gel and transferred to a Nylon filter in 10×SCP (20 SCP: 2M NaCl, 0.6 M disodium phosphate, 0.02 M disodium EDTA) according to standard methods (Southern, 1975). Locus DNA or RNA sequences are labeled, for example, radioactively with $^{32}P$ by random priming (Feinberg & Vogelstein, 1983). Filters are prehybridized in 6×SCP, 10% dextran sulfate, 2% sarcosine, and 500 µg/ml denatured salmon sperm DNA. The labeled probe is denatured, hybridized to the filter and washed in 2×SCP, 1% SDS at 65° for 30 minutes and visualized by autoradiography using Kodak XAR5 film. Presence of the locus is indicated by detection of restriction fragments of the appropriate size.

IV. Tissue Cultures and In Vitro Regeneration of *Sorghum* Plants

A further aspect of the invention relates to tissue cultures of the *sorghum* plant designated Tx3361. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, kernels, leaves, stalks, roots, root tips, anthers, and the like. In a one embodiment, the tissue culture comprises embryos, protoplasts, meristematic cells, pollen, leaves or anthers derived from immature tissues of these plant parts. Means for preparing and maintaining plant tissue cultures are well known in the art (U.S. Pat. No. 4,666,844; U.S. Pat. No. 5,538,880; U.S. Pat. No. 5,550,318; and U.S. Pat. No. 6,369,298; each incorporated herein by reference in their entirety). By way of example, a tissue culture comprising organs such as anthers has been used to produce regenerated plants (Rose et al., 1986; Kumaravadivel and Rangasamy, 1994; U.S. Pat. No. 5,445,961 and U.S. Pat. No. 5,322,789; the disclosures of which are incorporated herein by reference).

One type of tissue culture is anther culture. Anthers enclose microspores that develop into pollen. For anther/microspore culture, microspores can be selected at a stage when they are uninucleate, that is, include only one, rather than 2 or 3 nuclei. Methods to determine the correct stage are well known to those skilled in the art and include mitramycin fluorescent staining, trypan blue and acetocarmine squashing. The mid-uninucleate microspore stage has been found to be the developmental stage most responsive to the subsequent methods disclosed to ultimately produce plants.

Although microspore-containing plant organs can generally be pretreated at any cold temperature below about 25° C., a range of 4 to 25° C. may be used, and specifically a range of 8 to 14° C. Although other temperatures yield embryoids and regenerated plants, cold temperatures produce optimum response rates compared to pretreatment at temperatures outside these ranges. Response rate is measured as either the number of embryoids or the number of regenerated plants per number of microspores initiated in culture. Exemplary methods of microspore culture are disclosed in, for example, Rose et al., 1986; Kumaravadivel and Rangasamy, 1994; U.S. Pat. No. 5,322,789 and U.S. Pat. No. 5,445,961, the disclosures of which are specifically incorporated herein by reference.

In one embodiment, it is generally preferred to sterilize their surface. Following surface sterilization, for example, with a solution of calcium hypochloride, the anthers are removed from about 70 to 150 spikelets and placed in a preculture or pretreatment medium. Larger or smaller amounts can be used depending on the number of anthers.

To isolate microspores, an isolation media may be used. An isolation media is used to separate microspores from the anther walls while maintaining their viability and embryogenic potential. An illustrative embodiment of an isolation media includes a 6% sucrose or maltose solution combined with an antioxidant such as 50 mg/l of ascorbic acid, 0.1 mg/l biotin, and 400 mg/l of proline, combined with 10 mg/l of nicotinic acid and 0.5 mg/l $AgNO_3$. In another embodiment, the biotin and proline are omitted.

An isolation media can have a higher antioxidant level where it is used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably, from about 50 mg/l to about 100 mg/l.

One can find particular benefit in employing a support for the microspores during culturing and subculturing. Any support that maintains the cells near the surface can be used. An illustrative embodiment of a solid support is a TRAN- SWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent).

The liquid medium passes through the mesh while the microspores are retained and supported at the medium-air interface. The surface tension of the liquid medium in the petri dish causes the raft to float. The liquid is able to pass through the mesh; consequently, the microspores stay on top. The mesh remains on top of the total volume of liquid medium.

The culture vessels can be further defined as either (1) a bilayer 60 mm petri plate wherein the bottom 2 ml of medium are solidified with 0.7% agarose overlaid with 1 mm of liquid containing the microspores; (2) a nylon mesh raft wherein a wafer of nylon is floated on 1.2 ml of medium and 1 ml of isolated microspores is pipetted on top; or (3) TRAN-SWELL® plates wherein isolated microspores are pipetted onto membrane inserts which support the microspores at the surface of 2 ml of medium.

Examples of processes of tissue culturing and regeneration of *sorghum* are described in, for example, Rose et al., 1986; Kumaravadivel and Rangasamy; Wen et al., 1991; and Ma et al., 1987.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production and Analysis of *Sorghum*×Sugarcane Hybrids

Seed of line Tx3361 was planted in pots in the greenhouse from mid-July through mid-September so that anthesis would match with sugarcane anthesis. At the onset of anthesis, male sterile plants of Tx3361 were identified and bagged based on anther phenotype. *Sorghum*×sugarcane pollinations were made at the USDA-ARS Sugarcane Research Unit in Houma, La. between late September and early November of 2007 and 2008. Additional pollinations were made in College Station, Tex. in January and February. A total of 67 basic and commercial sugarcane breeding lines were used as male parents.

Pollinations made in Houma were completed by dusting the *sorghum* panicle with sugarcane pollen and rubbing the *sorghum* panicle through the sugarcane tassel. In the following year, crosses were made by placing one to three *sorghum* panicles with a single sugarcane parent and tapping the sugarcane tassels followed by rubbing the *sorghum* panicles into the sugarcane tassels. This process was repeated for three or four consecutive days. Upon completion of these crosses, pollinated *sorghum* plants were returned to College Station for seed development and maturation. For the *sorghum*×sugarcane crosses made in College Station each *sorghum* panicle was pollinated one time; pollinations were made using the same methodology practiced in Houma in the prior year.

Seed Preparation

Seeds were removed from the maternal parent on average at 46, 41, and 27 days post pollination over three years respectively. Seed from the first year were stored from 30 to 90 days prior to germination while seed from the following years were germinated immediately after harvest. The timeline for harvest and germination was decreased due to the high frequency of vivipary in the seed. After harvest and prior to germination, seeds were surface sterilized by first coating them with a liquid suspension of Captan and Apron for at least half an hour and then immersing them in a 30% solution of bleach for 20 minutes. After surface sterilization the seeds were rinsed in sterile water and placed embryo side up in a petri dish containing a culture medium of Murashige-Skoog (Murashige and Skoog, 1962) basal salts and vitamins supplemented with 10 mg L-1 glycine, 10 mg L-1 L-arginine-HCl, 10 mg L-1 L-tyrosine, 100 mg L-1 inositol, and 30 g L-1 sucrose, solidified with 0.7% agar (plant tissue culture grade, Phytotechnology Laboratories, Shawnee Mission, Kans.) (Sharma, 1999). All petri dishes were sealed with Parafilm and placed under grow lights set to 14 hour days with a constant temperature between 27 and 30° C. All seeds that showed good development in both the root and shoot were potted in 4" pots. Once established, they were transferred to the greenhouse.

Confirmation of Intergeneric Hybrid Plants

Intergeneric hybrids were initially classified by morphology. As they developed, all hybrids exhibited numerous characteristics of sugarcane (height, tillering, maturity) that the maternal parent did not possess, in addition to having traits not passed by the paternal parent. These plants were confirmed as intergeneric hybrids by somatic chromosome number. Chromosome spreads were prepared from root tips using a method described by Jewell and Islam-Faridi (1994) with the following modifications. Young actively growing root tips were pretreated with a saturated aqueous solution of α-bromonaphthalene for 2.75 hours at room temperature and fixed overnight in 3:1 95% ethanol/glacial acetic acid (3:1 v/v). Root tips were then rinsed several times with distilled water, hydrolyzed for 10 min in 0.2 M HCl and rinsed 10 minutes in distilled water. Cell walls were digested with an aqueous solution of 5% cellulase (Onozuka R-10, Yakult Honsha Co. Ltd., Tokyo) and 1.0% pectolyase Y-23 (Seishin Corporation, Tokyo) at pH 4.5 for 35 to 60 minutes at 37° C. and rinsed three times with distilled water. Meristems were placed on a clean glass slide in an ethanol/glacial acetic acid (3:1) solution, macerated, and spread with fine-tipped forceps, air-dried at room temperature for 2 days, and stained with Azure Blue. Root tip spreads were examined using a Zeiss Universal II microscope (Carl Zeiss Inc., Gottingen, Germany) with 63× and 100× apochromat objectives. Images were captured with an Optronics VI-470 system (Optronics Inc., Goleta, Calif.)

and digitally stored and processed with Optimas (v. 6.1) image analysis software (Optimas Corp., Bothell, Wash.).

Effect of Sugarcane Pollinator on Hybrid Seed Set

For each cross made in Houma in the second year, the sugarcane parent, date of pollination, location of pollination, pollen load, florets/panicle, seeds/panicle and seedlings produced were recorded. Sugarcane pollen load was a subjective measurement determined at the time hybrid seed was harvested by evaluating the dried stigmas under a dissecting scope and rating them as light, medium or heavy; light meant little or no pollen observable; medium rank was assigned if pollen was observed on a number of the stigmas while a heavy rank was assigned if thorough coverage was observed. For each cross made in College Station in the third year the sugarcane parent, date of pollination, seeds/panicle and seedlings produced were recorded.

To determine relative effect of location, date of pollination and sugarcane pollinator on seed set and pollen load, PROC GLM in SAS v9.1 was used. Only sugarcane males that had been used in at least three pollinations were included in the analysis. All effects were considered fixed and only interactions involving the pollinator were included in the analysis of variance.

2007 Hybrid Seed Production, Confirmation and Growth

In the fall of 2007 (first year), a total of 24 pollinations were made using 17 different pollinators (Table 3). Based on stigma reaction, it was apparent that fertilization had occurred after pollination. Seed began to develop, although size and rate of growth was reduced compared to normal *sorghum* self or cross-pollination. When the seed was prepared for germination (after harvest and storage, it was evident embryo loss during seed development and vivipary after development was common; further analysis revealed that 32% were viviparous and 39% had no embryo. A fair proportion of the remaining seed germinated and produced plants. All of these plants were intergeneric hybrids and they reflected a wide range of phenotypes, from very poor in growth to highly vigorous.

From these pollinations, 23 of the best hybrids were transplanted into pots in the greenhouse. All of these plants had morphological features similar to sugarcane. Somatic chromosome counts for these hybrids ranged from 56 to 64; 10 chromosomes were from *sorghum* and the rest of the chromosomes were from *Saccharum*. The hybrids have long narrow and numerous leaves compared to Tx3361, which has fewer leaves that are shorter and broader. Upon development the 23 hybrids displayed a wide range of vigor and growth habit; two of these hybrids displayed excellent growth and development. These hybrids were vigorous and tillered much like sugarcane although each had morphological traits unique to *sorghum* such as nodal brace roots and/or excessive waxy bloom on leaf sheaths. In seven months, canes of hybrid L07-11S were 3.1 m while canes of hybrid L07-9S were 2.7 m. Both of these hybrids were photoperiod sensitive like sugarcane, flowering from mid December through January in College Station whereas Tx3361 flowers in approximately 65 days regardless of planting date. The panicles on these hybrids were slightly more compact than those of sugarcane; attempts to testcross confirmed both male and female sterility of these two particular hybrids. In August, several canes of both hybrids were cut to test for vegetative propagation and sugar distribution. Vegetative propagation was successful and sugar concentration in these hybrids was similar to the pattern found in sugarcane with increasing sugar concentrations in the more mature internodes (Whittaker and Botha, 1997).

Further Hybrid Seed Production and Enhancement of Process (2008/2009)

In 2008 a total of 155 *sorghum* panicles (totaling 74,300 florets) were pollinated. From these pollinations, 10,347 seed were recovered, resulting in an average seed set of 14%. Percent seed set was not measured in the 2009 pollinations, but it appeared similar to that observed in 2008. However germination was substantially improved between the 2008 and 2009 pollinations because seed was harvested earlier and losses due to vivipary were avoided. In 2009, germination increased from 2008 to 2009 because seed were harvested earlier (28 days post pollination versus 40 days post pollination) to avoid losses due to vivipary. In addition, 2008 germination was further reduced by the embryo's inability to grow through the seed coat; hence, in all of the 2009 seed the pericarp was removed prior to plating on media. As the technique improved, germination rates improved from 2.5% in 2007 to 5.7% in 2008 to 33% in 2009.

TABLE 3

Sugarcane Parents Used in the *Sorghum* × Sugarcane Crosses

| Male | Panicles | Florets | Seed no. | Seedlings | Field Test |
|---|---|---|---|---|---|
| Houma Pollinators 2007 | | | | | |
| Example 2007 Males | | | | | |
| Ho00-961 | 1 | | 4 | 1 | |
| HoCP01-517 | 1 | | 8 | 1 | |
| HoCP04-838 | 1 | | 59 | 2 | 1 |
| HoCP96-540 | 1 | | 46 | 2 | |
| 2007 Totals | 24 | | 1504 | 23 | 2 |
| Houma Pollinators 2008 | | | | | |
| Example 2008 Males | | | | | |
| Erianthus | 1 | 544 | 0 | 0 | 0 |
| Ho01-564 | 5 | 3,275 | 334 | 16 | 1 |
| Ho05-961 | 23 | 8,976 | 1,691 | 160 | 88 |
| Ho06-525 | 6 | 2,765 | 301 | 19 | 10 |
| Ho06-530 | 1 | 975 | 0 | 0 | 0 |
| Ho06-543 | 2 | 592 | 9 | 1 | 0 |
| Ho06-552 | 2 | 978 | 10 | 0 | 1 |
| Ho06-562 | 4 | 1,725 | 480 | 13 | 0 |
| Ho06-563 | 1 | 281 | 85 | 3 | 2 |
| Ho06-565 | 2 | 408 | 199 | 0 | 0 |
| Ho07-613 | 2 | 1,131 | 316 | 1 | 0 |
| Ho95-988 | 1 | 760 | 43 | 0 | 0 |
| HoCP01-517 | 5 | 2,506 | 217 | 14 | 5 |
| HoCP04-803 | 1 | 393 | 19 | 1 | 0 |
| HoCP04-810 | 2 | 1,120 | 10 | 0 | 0 |
| HoCP04-838 | 8 | 5,152 | 603 | 91 | 46 |
| HoCP05-903 | 2 | 894 | 72 | 0 | 0 |
| HoCP05-904 | 3 | 2,074 | 581 | 34 | 19 |
| HoCP05-923 | 3 | 951 | 4 | 2 | 0 |
| HoCP06-502 | 1 | 159 | 13 | 0 | 0 |
| HoCP96-540 | 11 | 6,934 | 929 | 86 | 12 |
| HoL05-953 | 1 | 240 | 22 | 0 | 0 |
| L01-283 | 9 | 4,972 | 1,301 | 36 | 7 |
| L06-001 | 1 | 795 | 31 | 3 | 0 |
| L06-024 | 3 | 1,260 | 669 | 40 | 16 |
| L06-38 | 2 | 872 | 32 | 0 | 0 |
| L99-226 | 2 | 592 | 5 | 1 | 0 |
| L99-266 | 1 | 475 | 90 | 21 | 2 |
| LCP85-384 | 3 | 1,937 | 145 | 11 | 3 |
| US02-840 | 1 | 557 | 2 | 0 | 0 |
| 2008 Totals | 155 | 74,743 | 10,347 | 592 | 217 |
| Texas Pollinators 2009 | | | | | |
| TCP00-4521 | 16 | | 28 | 9 | 5 |
| TCP01-4535 | 7 | | 66 | 32 | 13 |
| TCP02-4622 | 11 | | 362 | 128 | 23 |

TABLE 3-continued

Sugarcane Parents Used in the Sorghum × Sugarcane Crosses

| Male | Panicles | Florets | Seed no. | Seedlings | Field Test |
|---|---|---|---|---|---|
| TCP03-4636 | 30 | | 1,651 | 519 | 215 |
| TCP03-4645 | 9 | | 203 | 68 | 12 |
| Total | 73 | | 2,310 | 756 | 268 |
| Grand Total | 252 | 74,743 | 14,161 | 1371 | 487 |

From the combined 2008/2009 pollinations, a total of 1348 seedlings were potted and transferred to the greenhouse. The phenotypic variation present in these hybrids was extensive, but all were morphologically more like sugarcane than *sorghum*. In the spring of 2009, 485 hybrids were selected (based on vigor) and transplanted into a space-plant nursery near College Station (Table 3). These hybrids are expected to follow growth and development patterns observed in the limited set of hybrids evaluated from the 2007 crosses.

Effect of Pollinator Parent on Seed Set and Germination

Analysis of variance detected a significant effect on seed set due to pollinator parent (Table 4). The range of variation due to pollinator clearly indicates that certain sugarcane varieties are better pollinators for the production of intergeneric hybrids on Tx3361. Sugarcane pollinators such as L06-024, HoCP05-904 and Ho06-562 demonstrate the most effective hybrid seed production (Table 5).

TABLE 4

Analysis of variance for seed set and pollen load for seventeen sugarcane pollinators used to pollinate Tx3361 in Houma, La in the fall of 2008

| | Seed Set | | | Pollen Load | | |
|---|---|---|---|---|---|---|
| Source | df | MS | Pr > F | df | MS | Pr > F |
| Location | 3 | 0.031 | 0.216 | 3 | 0.655 | 0.093 |
| Date(Location) | 14 | 0.025 | 0.283 | 15 | 0.631 | 0.019 |
| Male | 16 | 0.047 | 0.010 | 16 | 0.877 | 0.001 |
| Male*Location | 10 | 0.022 | 0.381 | 10 | 0.285 | 0.474 |
| Male*Date(Location) | 8 | 0.031 | 0.167 | 9 | 0.739 | 0.016 |
| Error | | | | | | |

TABLE 5

Number of pollinations, Percent seed set on Tx3361 and pollinator pollen load for 17 different sugarcane cultivars and/or breeding lines in the fall of 2008 in Houma, La

| Sugarcane Pollinator* | Pollinations no. | Seed set % | Pollen load** |
|---|---|---|---|
| L06-024 | 3 | 53.0 | 2.33 |
| HoCP05-904 | 3 | 36.0 | 2.67 |
| Ho06-562 | 4 | 25.2 | 2.50 |
| L01-283 | 9 | 24.9 | 2.00 |
| Ho05-961 | 23 | 18.2 | 1.65 |
| HB03-403 | 5 | 15.6 | 1.80 |
| HoCP04-838 | 8 | 15.3 | 2.10 |
| HoCP96-540 | 11 | 13.6 | 1.64 |
| HoCP01-517 | 5 | 10.1 | 1.40 |
| Ho01-564 | 5 | 8.9 | 1.40 |
| Ho06-525 | 5 | 8.6 | 1.80 |
| MPTH97-209 | 4 | 8.2 | 2.00 |
| LCP85-384 | 3 | 7.5 | 3.00 |
| US07-9014 | 7 | 5.7 | 1.86 |
| US079026 | 7 | 0.7 | 1.00 |
| US079025 | 3 | 0.6 | 1.67 |
| HoCP05-923 | 3 | 0.4 | 1.00 |
| Mean | | 14.8 | 1.80 |
| L.S.D. | | 18.5 | 0.70 |

*Only pollinators that were used in at least three pollinations were included in this analysis;
**Pollen load rating were 1 (light), 2 (medium) and 3 (heavy).

It has been known that pollen shed in sugarcane is influenced by genotype and environment (Moore and Nuss, 1987) and analysis of variance confirmed that pollen load was influenced by pollinator parent as well as date of pollination (Table 4). Lines with low pollen load consistently produced crosses with low seed set, but high pollen load did not necessarily indicate a high seed set. Six of the top seven sugarcane pollinators (defined by seed set percentage) had average or above average pollen load while males with below average seed set varied in pollen load (Table 5). These results imply that males must not only produce good pollen but that they must also have favorable genetic and/or genomic compatibility with Tx3361.

Analysis of variance of 2009 data indicated that neither pollination environment nor sugarcane pollinator influenced percent germination. Based on the current technology for managing seed production and germination, it is reasonable to expect between 25-40% of those seed to germinate and produce plants regardless of which pollinator is used and where the pollination is made.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 3,710,511
U.S. Pat. No. 3,861,709
U.S. Pat. No. 4,654,465
U.S. Pat. No. 4,666,844
U.S. Pat. No. 4,727,219
U.S. Pat. No. 4,769,061
U.S. Pat. No. 4,810,648
U.S. Pat. No. 4,936,904

U.S. Pat. No. 4,940,835
U.S. Pat. No. 4,975,374
U.S. Pat. No. 5,302,532
U.S. Pat. No. 5,322,789
U.S. Pat. No. 5,371,003
U.S. Pat. No. 5,384,253
U.S. Pat. No. 5,445,961
U.S. Pat. No. 5,464,765
U.S. Pat. No. 5,492,547
U.S. Pat. No. 5,530,191
U.S. Pat. No. 5,538,880
U.S. Pat. No. 5,550,318
U.S. Pat. No. 5,591,616
U.S. Pat. No. 5,625,132
U.S. Pat. No. 5,684,242
U.S. Pat. No. 5,689,041
U.S. Pat. No. 5,736,369
U.S. Pat. No. 5,736,369
U.S. Pat. No. 5,741,684
U.S. Pat. No. 6,040,497
U.S. Pat. No. 6,369,298
U.S. Pat. No. 6,762,344
Abe et al., *J. Biol. Chem.*, 262:16793, 1987.
Armstrong and Green, *Planta*, 164:207-214, 1985.
Arondel et al., *Science*, 258(5086):1353-1355 1992.
Beachy et al., *Ann. Rev. Phytopathol.*, 28:451, 1990.
Casas, et al., *PNAS*, 90:11212-11216, 1993.
Chang, In *Plant Breeding in the 1990s*, Stalker and Murphy (Eds.), Wallingford, U.K., CAB International, 17-35, 1992.
Conger et al., *Plant Cell Reports*, 6:345-347, 1987.
DeGreef et al., *Biotechnology*, 7:61, 1989.
Duncan et al., *Planta*, 165:322-332, 1985.
Elliot et al., *Plant Molec. Biol.*, 21:515, 1993.
European Appln. 0160390
European Appln. 0242246
European Appln. 0333033
European Appln. 0616644
European Appln. 534 858
European Appln. 672752
Fehr, *Principles of Cultivar Development*, 1:360-376, 1987.
Feinberg & Vogelstein, *Anal. Biochem.*, 132(1):6-13, 1983.
Fisher et al., *Plant Physiol.*, 102:1045, 1993.
Fox et al. *Proc. Natl. Acad. Sci. USA*, 90(6):2486-2490, 1993.
Gaillard et al., *Plant Cell Reports*, 10(2):55, 1991.
Gleen et al., *Plant Molec. Biology*, 18:1185-1187, 1992.
Gordon-Kamm et al., *The Plant Cell*, 2:603-618, 1990.
Green and Rhodes, *Maize for Biological Research*, 367-372, 1982.
Hammock et al., *Nature*, 344:458, 1990.
Hayes et al., *Biochem. J.*, 285 (Pt 1):173-180, 1992.
Huub et al., *Plant Molec. Biol.*, 21:985, 1993.
Jones et al., *Science*, 266:7891, 1994.
Kirihara et al., *Gene*, 71(2):359-370, 1988.
Knutzon et al., *Proc. Natl. Acad. Sci. USA*, 89:2624, 1992.
Kumaravadivel and Rangasamy, *Plant Cell Reports*, 13:286-290, 1994.
Laurie, D. A. and M. D. Bennett, *Ann. Bot.*, 64:675-681, 1989.
Lee et al., *EMBO J.*, 7:1241, 1988.
Logemann et al., *Biotechnology*, 10:305, 1992.
Ma et al., *Theor. Appl. Genet.*, 73:389-394, 1987.
Marshall et al., *Theor. Appl. Genet.*, 83:4:35, 1992.
Martin et al., *Science*, 262: 1432, 1993.
McDonough et al., *J. Biol. Chem.*, 267(9):5931-5936, 1992.
Miki et al., *Theor. Appl. Genet.*, 80:449, 1990.
Mindrinos et al., *Cell*, 78(6):1089-1099, 1994.
Omirulleh et al., *Plant Mol. Biol.*, 21(3):415-428, 1993.
Pace et al., *Theoretical and Applied Genetics*, 73:863-869, 1987.
PCT Appln. US93/06487
PCT Appln. WO 91/13972
PCT Appln. WO 95/06128
PCT Appln. WO 98/44140
Pedersen and Toy, *Crop Science*, 37(6):1973-1975, 1997.
Pen et al., *Biotechnology*, 10:292, 1992.
Poehlman et al., In: *Breeding Field Crops*, 4$^{th}$ Ed., Iowa State University Press, Ames, Iowa, 132-155; 321-344, 1995.
Przibila et al., *Plant Cell*, 3:169, 1991.
Rao et al., In: *Somatic Embryogenesis in Glume Callus Cultures*, Maize Genetics Cooperation Newsletter #60, 1986.
Reddy et al., *Plant Mol. Biol.*, 22(2):293-300, 1993.
Rooney et al., *Biofuels, Bioproducts and Biorefining.*, 1:147-157, 2007.
Rose et al., *Plant Cell Tissue Organ Culture*, 6:15-22, 1986.
Sambrook et al., In: *Molecular cloning*, Cold Spring Harbor Laboratory Press, Cold Spring Harbor, N.Y., 2001.
Sergaard et al., *J. Biol. Chem.*, 268:22480, 1993.
Shiroza et al., *J. BacteoL.*, 170:810, 1988.
Shure et al., *Cell*, 35(1):225-233, 1983.
Songstad et al., *Plant Cell Reports*, 7:262-265, 1988.
Southern, *J. Mol. Biol.*, 98:503-517, 1975.
Sprague and Dudley, In: *Corn and Corn Improvement*, 3$^{rd}$ Ed., Crop Science of America, Inc.; Soil Science of America, Inc., Wisconsin. 881-883; 901-918, 1988.
Steinmetz et al., *Mol. Gen. Genet.*, 20:220, 1985.
Sumitani et al., *Biosci. Biotech. Biochem.*, 57:1243, 1993.
Tavladoraki et al., *Nature*, 366:469, 1993.
Taylor et al., Seventh Inn Symposium on Molecular Plant-Microbe Interactions, Edinburgh, Scotland, Abstract W97, 1994.
Van Damme et al., *Plant Molec. Biol.*, 24:25, 1994.
Van Hartingsveldt et al., *Gene*, 127:87, 1993.
Wang et al., *Science*, 280:1077-1082, 1998.
Wen et al., *Euphytica*, 52:177-181, 1991.
Williams et al., *Nucleic Acids Res.*, 18:6531-6535, 1990.

What is claimed is:

1. A cell of sorghum line Tx3361, representative seed of said line having been deposited under ATCC Accession No. PTA-10149.

2. A plant of sorghum line Tx3361, representative seed of said line having been deposited under ATCC Accession No. PTA-10149.

3. A plant part of the plant of claim 2.

4. The plant part of claim 3, further defined as a protoplast, cell, meristem, root, pistil, anther, flower, embryo, stalk or petiole.

5. A tissue culture of regenerable cells according to claim 1.

6. A sorghum plant regenerated from the tissue culture of claim 5, wherein the regenerated sorghum plant expresses all of the physiological and morphological characteristics of the sorghum line Tx3361.

7. A method of producing seed, comprising crossing the plant of claim 2 with itself or a second plant.

8. The method of claim 7, wherein the second plant is a distinct sorghum plant.

9. The method of claim 7, wherein the second plant is a plant of a genus other than *Sorghum*.

10. The method of claim 7, wherein the second plant is a plant of a species other than *Sorghum bicolor*.

11. A method of producing a plant of sorghum line Tx3361 comprising an added desired trait, the method comprising introducing a transgene conferring the desired trait into the plant of claim 2.

12. The method of claim 11, wherein the desired trait is selected from the group consisting of male sterility, herbicide tolerance, insect or pest resistance, disease resistance, modified fatty acid metabolism, modified carbohydrate metabolism, drought tolerance, increased biomass, as well as enhanced sugar production, sugar content and cellulose content.

13. The method of claim 12, wherein the desired trait is herbicide tolerance and the tolerance is conferred to an herbicide selected from the group consisting of glyphosate, sulfonylurea, imidazalinone, dicamba, glufosinate, phenoxy proprionic acid, cyclohexanedione, triazine, benzonitrile and broxynil.

14. The method of claim 11, wherein the desired trait is insect resistance and the transgene encodes a *Bacillus thuringiensis* (Bt) endotoxin.

15. A plant produced by introducing a transgene conferring a desired trait into the plant of claim 2, wherein the produced plant comprises the desired trait and otherwise comprises all of the physiological and morphological characteristics of sorghum line Tx3361 when grown in the same environmental conditions.

16. A method of introducing a single locus conversion into sorghum line Tx3361 comprising:
  (a) crossing the plant of claim 3 with a second plant to produce sorghum seed, wherein the second plant comprises a desired single locus;
  (b) growing $F_1$ progeny plants from the seed and selecting at least a first $F_1$ progeny plant that has the single locus to produce selected progeny plants;
  (c) crossing the selected progeny plants with at least the plant of claim 3 to produce backcross progeny plants;
  (d) selecting backcross progeny plants that have the single locus and physiological and morphological characteristics of sorghum line Tx3361 to produce selected backcross progeny plants; and
  (e) repeating steps (c) and (d) one or more times in succession to produce selected second or higher backcross progeny plants that comprise the single locus and otherwise comprise all of the physiological and morphological characteristics of sorghum line Tx3361 when grown in the same environmental conditions.

17. The method of claim 16, wherein the single locus confers a trait selected from the group consisting of male sterility, herbicide tolerance, insect or pest resistance, disease resistance, modified fatty acid metabolism, modified carbohydrate metabolism, drought tolerance, increased biomass, as well as enhanced sugar production, sugar content and cellulose content.

18. The method of claim 17, wherein the trait is tolerance to an herbicide selected from the group consisting of glyphosate, sulfonylurea, imidazalinone, dicamba, glufosinate, phenoxy proprionic acid, cyclohexanedione, triazine, benzonitrile and broxynil.

19. The method of claim 17, wherein the trait is insect resistance and the insect resistance is conferred by a transgene encoding a *Bacillus thuringiensis* endotoxin.

20. The plant of claim 2, further defined as comprising a single locus conversion, wherein the plant otherwise comprises all of the physiological and morphological characteristics of sorghum line Tx3361 when grown in the same environmental conditions.

21. A method of producing an inbred sorghum plant derived from the sorghum variety Tx3361, the method comprising the steps of:
  (a) obtaining sorghum seed according to the method of claim 16 and growing at least a first seed to produce a progeny plant;
  (b) crossing the progeny plant with itself or a second plant to produce a seed of a progeny plant of a subsequent generation;
  (c) growing a progeny plant of a subsequent generation from said seed and crossing the progeny plant of a subsequent generation with itself or a second plant; and
  (d) repeating steps (b) and (c) for an additional 3-10 generations with sufficient inbreeding to produce an inbred sorghum plant derived from the sorghum line Tx3361.

22. A commodity plant product comprising at least a first cell according to claim 1.

23. The commodity plant product of claim 22, wherein the commodity plant product is syrup, seed oil, or protein.

* * * * *